(12) United States Patent
Rodriguez et al.

(10) Patent No.: US 6,329,557 B1
(45) Date of Patent: Dec. 11, 2001

(54) PURIFICATION OF XANTHOPHYLLS FROM MARIGOLD EXTRACTS THAT CONTAIN HIGH LEVELS OF CHLOROPHYLLS

(75) Inventors: Gustavo Rodriguez, Sinaloa; Mario-David Torres-Cardona, Nuevo Leon; Alejandro Diaz, Sinaloa, all of (MX)

(73) Assignee: Prodemex, S.A. de C.V., Sinaloa (MX)

( * ) Notice: Subject to any disclaimer, the term of this patent is extended or adjusted under 35 U.S.C. 154(b) by 0 days.

(21) Appl. No.: 09/590,611

(22) Filed: Jun. 9, 2000

(51) Int. Cl.$^7$ ............................. C07C 35/08; C07C 1/00
(52) U.S. Cl. ........................ 568/834; 554/12; 568/816; 568/822; 568/827; 568/832
(58) Field of Search ..................................... 568/834, 832, 568/824, 823, 822, 816; 554/12

(56) References Cited

U.S. PATENT DOCUMENTS

| | | |
|---|---|---|
| 4,048,203 | 9/1977 | Philip . |
| 5,382,714 | 1/1995 | Khachik . |
| 5,523,494 | 6/1996 | Torres-Cardona et al. . |
| 5,648,564 | 7/1997 | Ausich et al. . |
| 5,973,211 | 10/1999 | Rodriguez . |
| 6,191,293 * | 2/2001 | Levy ...................................... 554/12 |

FOREIGN PATENT DOCUMENTS

| | | |
|---|---|---|
| 0 732 378 | 9/1996 | (EP) . |
| WO 99/20587 | 4/1999 | (WO) . |

* cited by examiner

*Primary Examiner*—Charanjit S. Aulakh
(74) *Attorney, Agent, or Firm*—Knobbe, Martens, Olson & Bear, LLP

(57) ABSTRACT

The present invention provides an industrial scale process for obtaining lutein and zeaxanthin concentrates of high purity from saponified marigold extracts that may have high levels of chlorophyll.

24 Claims, No Drawings

PURIFICATION OF XANTHOPHYLLS FROM MARIGOLD EXTRACTS THAT CONTAIN HIGH LEVELS OF CHLOROPHYLLS

BACKGROUND OF THE INVENTION

1. Field of the Invention

The present invention relates to a process for purifying lutein and zeaxanthin from crude marigold extracts that may contain high levels of chlorophyll pigments.

2. Description of the Related Art

The carotenoids comprise a group of natural pigments found abundantly in plants, some fish, crustaceans, birds, algae and bacteria. Within this group of pigments are the yellow carotenoids, including both the carotenes (e.g., β-carotene) and xanthophylls (e.g., lutein and zeaxanthin), and the red carotenoids, including capsanthin, canthaxanthin and astaxanthin. These yellow and red carotenoids are often present in plants, especially flowering plants, together with other classes of pigments, including primarily green chlorophyll pigments.

Carotenoids and in particular, xanthophylls, from marigold extracts have been used for decades in the poultry industry for pigmentation of broiler skins and egg yolks. Lutein, is present at much higher concentrations than zeaxanthin in marigold extracts. Pigmenting formulations for use in the poultry industry having relatively high concentrations of zeaxanthin have recently appeared on the market, wherein the lutein has been isomerized to yield zeaxanthin (U.S. Pat. No. 5,523,494 to Torres and U.S. Pat. No. 5,973,211 to Rodriguez).

In addition to their commercial importance in the poultry industry, the carotenoids have recently received considerable attention from scientists with respect to their potential role in promoting human health. Compounds like α and β-carotene, lutein and zeaxanthin have been shown to possess strong antioxidant activity, which may retard or prevent diseases like cancer, arteriosclerosis, cataracts, macular degeneration and others (Bowen, WO98/45241). Lutein and zeaxanthin are the only carotenoids present in the macular region of the human retina and are related to the normal function of the macula responsible for visual acuity. It has also been reported that carotenoids enhance the immune response. Free radicals produced as byproducts of metabolic processes and originating from environmental pollutants (such as nitrogen dioxide and ozone of polluted air, heavy metals, halogenated hydrocarbons, ionizing radiation and cigarette smoke) are implicated as causative factors in many of the above-mentioned diseases. Carotenoids are potent quenchers of the highly reactive oxygen free radicals that can initiate a cascade of detrimental chemical reactions. Carotenoids also function as chain-breaking antioxidants, especially at low partial pressures of oxygen. Thus, carotenoids can work to quench free radical-induced reactions and can also prevent generation of free radicals, thereby limiting free radical/oxidative damage.

Hand-picked marigold petals from *Tagetes erecta* contain one of the highest concentrations of carotenoids found in nature. Industrial scale culture of marigolds and mechanization of the harvesting process have increased the amount of harvested leaves, stems, weeds and other plant parts that are typically obtained along with the flower petals. Oleoresins with high levels of chlorophylls and related compounds are obtained when meals from such raw material are extracted. Consequently, the lutein and zeaxanthin concentrations are relatively lower in such oleoresins than in those obtained from hand picked flowers.

The marigold extracts with high chlorophyll content are normally saponified under alkaline conditions to complete hydrolysis of the carotenoids as well as the chlorophyll. Variable levels of other lipids, chlorophyllins and unsaponifiable matter are also normally present in the reaction mixture. Consequently, the relatively low concentration of xanthophylls in oleoresins from mechanically harvested marigold meals, as well as the variability in levels of contaminating pigments, have impeded the commercial development of xanthophyll products for human consumption. Thus, there remains a need for an industrial process for obtaining lutein and zeaxanthin concentrates of high purity from meals prepared from large-scale, mechanically-harvested marigold cultures, which may have high levels of chlorophyll.

SUMMARY OF THE INVENTION

The present invention provides an industrial scale process for obtaining lutein and zeaxanthin concentrates of high purity using saponified marigold extracts that may have high levels of chlorophyll. It is also an objective of this invention to produce a xanthophyll concentrate, which may have applications for human use, wherein the levels of zeaxanthin and lutein are over 97% of the total carotenoids in the product.

More specifically, the present invention relates to a process for the purification of xanthophylls from a saponified extract. The process comprises the steps of dispersing the saponified extract in water to form a dispersion, mixing the dispersion under conditions such that a portion of any water-soluble compounds dissolves in the water to form an aqueous phase and a residue that is not soluble in water, separating the aqueous phase from the residue, contacting the residue with a nonpolar solvent under conditions such that a portion of any lipid-soluble compounds dissolves in the nonpolar solvent and a portion of the xanthophylls precipitates from the nonpolar solvent to form a precipitate, separating the nonpolar solvent from the precipitate, washing the precipitate with a polar solvent such that at least a portion of any remaining chlorophylls dissolves in the polar solvent, and separating the polar solvent from the precipitate to yield a product comprising the xanthophylls at a desired level of purity.

In one aspect of the invention, the saponified extract is obtained from mechanically-harvested marigolds comprising a mixture of carotenoids and chlorophylls.

In variations, the process may further comprise the steps of: recovering a substantial portion of any carotenoids from both the nonpolar and polar solvents; desolventizing and drying the product under inert atmosphere; and, adjusting the pH of the dispersion to between about 5.0 and 7.0, prior to mixing. The pH may be adjusted by adding an acid selected from the group consisting of phosphoric, sulfuric, hydrochloric, acetic or any mineral or organic acid of similar characteristics.

In further variations, the process may include the additional steps of: adjusting the dispersion to a temperature of between about 45° and 80° C. prior to mixing; and washing the residue with water prior to contacting the residue with the nonpolar solvent, wherein the water used for washing is adjusted to a pH of between about 5.0 and 7.0 and a temperature of between about 45° and 80° C.

In one aspect, the nonpolar solvent is selected from the group consisting of hexane, heptane, cyclohexane, octane, aromatic hydrocarbons, ethers and halogenated hydrocarbons, and the polar solvent is selected from the group consisting of a ketone, an alcohol, an amine, and mixtures thereof.

In another aspect, the xanthophylls in the product comprise a mixture of hydrolyzed lutein and zeaxanthin. The lutein and zeaxanthin may comprise greater than 95% of the carotenoids in the saponified extract. The product may also comprise between 400 to 900 grams of total carotenoids per kilogram of saponified extract. The saponified extract may comprise from about 0 to 20% chlorophylls. The concentration of carotenoids in the dispersion can be between about 0.1 to 15 grams per kilogram of the saponified extract, or more preferably between about 5 to 10 grams per kilogram of the saponified extract.

In another variation of the present process, the nonpolar solvent may be used in a proportion of between about 1 to 25 parts, and more preferably between about 5 to 12 parts, of solvent for each part of residue. The polar solvent may be used in a proportion of between 1 to 15 parts, and more preferably between about 4 to 10 parts, of solvent for each part of precipitate. The nonpolar and polar solvents may be used at ambient temperature.

In one aspect of the present invention, the product is suitable for administration to humans.

In another variation of the present invention, a process is disclosed for obtaining xanthophylls at a desired level of purity. The process comprises obtaining a saponified extract of a mechanically-harvested plant composition. The plant composition comprises a first plant part which comprises xanthophylls and a second plant part which comprises chlorophylls. The saponified extract is washed with water leaving an oily residue. The residue is contacted with a nonpolar solvent under conditions such that at least a portion of any lipid-soluble compounds dissolves in the nonpolar solvent and at least a portion of the xanthophylls precipitates from the nonpolar solvent to form a precipitate. The nonpolar solvent is separated from the precipitate. The precipitate is then washed with a polar solvent such that at least a portion of any remaining chlorophylls dissolves in the polar solvent. The polar solvent is separated from the precipitate to yield a product comprising the xanthophylls at the desired level of purity.

DETAILED DESCRIPTION OF THE PREFERRED EMBODIMENT

Numerous procedures are available for extraction and isolation of carotenoids from natural sources. For example, Philip (U.S. Pat. No. 4,048,203) discloses a process for purification of lutein in alcoholic media; Tyczhowski (*Poult. Sci.* 70(3):651–54) teaches isolation of free lutein from saponified marigold extracts by crystallization with different solvents; Ausich (U.S. Pat. No. 5,648,564) discloses isolation and purification of lutein from marigold extracts saponified in alkaline propylene glycol solutions, followed by crystallization; Khachik (U.S. Pat. No. 5,382,714) teaches isolation and purification of lutein from saponified marigold extracts by washing with alcohol/water mixtures at low temperature and then crystallizing in several binary solvent mixes also at low temperature. More recently, Khachik (WO 99/20587) discloses isolation and purification of lutein from several plant extracts saponified with alcoholic solutions of KOH and NaOH and using THF and water to extract and crystallize the carotenoids. By this process it is possible to separate chlorophyll present in the raw material from the carotenoids. Hills (U.S. Pat. No. 4,851,339) describes a process to simultaneously separate carotenes, tetrapyrroles and porphyrins especially in some algae.

Kitaoka (EP 732 378 A2) describes a process applicable to very dilute pigmenting extracts using liquid-liquid extractions with non polar solvents and aqueous solutions. Repeta (*Monogr. Oceanogr. Methodol.,* 1997, 10:239–60) makes a thorough review of a variety of methods for the purification of carotenoids for analytical and structure elucidation purposes, but not designed for commercial scale applications.

The present invention discloses processes for isolation and purification of lutein and zeaxanthin from natural sources, including in particular, marigold extracts that have relatively high levels of chlorophyll. More specifically, the raw materials for this process include saponified marigold extracts containing 20 g/kg or more of green matter. However, the disclosed processes are also considered applicable to the isolation and purification of xanthophylls from other sources of raw materials, having lower levels of contaminating chlorophyll pigments. Among the various sources of raw materials are algae, silkworm excrement, spinach and alfalfa leaves.

In one preferred embodiment of the present invention, marigold extracts containing from about 40 to about 150 grams of carotenoids per kilogram and from about 5 to about 20 grams of chlorophyll per kilogram are used as starting materials. Such extracts are produced by Productos Deshidratados de Mexico (PRODEMEX), Los Mochis, Sinaloa, Mexico. The marigold flowers used for making these extracts may be mechanically harvested, having significant amounts of leaves, stems, peduncles and other plant parts rich in chlorophyll and derivatives.

Marigold meals are prepared by dehydrating the machine-harvested flowers. There are several ways of dehydrating, including belt, tray, shelf and drum dryers or sun drying. The dry material is milled and the process is followed by a solvent extraction using a non-polar solvent, such as for example, hexane. The solvent is then removed by evaporation and a marigold oleoresin is obtained. The oleoresin is then saponified to complete hydrolysis of the xanthophylls and chlorophylls present. Saponification may be accomplished by treatment of the oleoresin with sodium or potassium hydroxide or some other alkali. The saponification conditions are well known to those of ordinary skill in the art.

Free lutein, zeaxanthin and other free xanthophylls are obtained during the saponification reaction, as well as sodium and potassium salts of fatty acids like myristic, palnitic and stearic acids. In addition, the phytyl and methyl groups on the pigment molecules may be substituted with sodium or potassium, depending on the base (e.g., NaOH or KOH, respectively) used as the saponifying agent. Water-soluble chlorophyllins may also be produced during saponification.

The saponified extract is then washed with water. The extract is dispersed in water and diluted to a final concentration of between about 0.1 to 30 grams of total xanthophylls per kilogram of the aqueous dispersion, preferably between about 5 to 10 grams per kilogram of aqueous dispersion. Preferably, the aqueous dispersion is mixed thoroughly to form a homogeneous mixture.

The pH of the mixture is then adjusted to between about 1.0 to 7.0, and preferably, between about 5.0 to 6.5, using aqueous solutions of an acid selected from the group consisting of acetic, phosphoric, sulfuric, hydrochloric or any inorganic or organic acid having similar characteristics. The concentration of the acid solution can be fixed from about 5 to 25% (w/w). The temperature of the mixture should be kept between about 20° to 80° C., and preferably, between about 45° to 70° C. The pH of the mixture is sufficiently decreased (neutralized) when the aqueous phase, which contains the water-soluble chlorophyllins and other water-soluble impurities, separates readily from the upper oily residue. The lower aqueous phase can be withdrawn using a conventional separatory apparatus. The oily residue contains some residual watersoluble chlorophyllins and the xanthophylls.

Additional water washes maintaining a fixed pH, may be used to reduce the concentration of residual water-soluble green matter from the oily upper phase. For each wash, it is possible to use from between 4 to 20 volumes of water to residue, but preferably, between 8 to 15 volumes of water per volume of residue. The water washings may be pooled for subsequent isolation of the green pigments. Water washing may be continued until the oily residue is essentially free of chlorophylls and related compounds and contains mainly lipids, water and xanthophylls.

The humid oily residue is then extracted with a nonpolar solvent. The solvent may be selected from the group consisting of short chain aliphatic (e.g., hexane) or aromatic hydrocarbons, alkyl-substituted solvents or a mixture thereof. Preferably, the hydrocarbons have between 6 to 8 carbon atoms. For each part of oily residue, between about 1 to 20 parts of nonpolar solvent (w/w) may be used, and preferably, between about 5 to 10 parts (w/w) for each extraction. Preferably, at least two extractions are used. The extractions are done at a temperature of between about –20° and 70° C., preferably between about 15° and 45° C., and more preferably between about 35° and 45° C. The lipids and carotenes, as well as other lipid-soluble substances, are extracted in the nonpolar solvent, which can be separated and pooled.

A solid that precipitates from the nonpolar solvent during the extraction is rich in lutein and zeaxanthin. Residual amounts of chlorophyll may still be present. One or two additional washes with a polar solvent should be sufficient to minimize the level of chlorophyll contamination. The polar solvent may be a ketone, alcohol, amine or any other polar solvent of similar nature. The solvent should be acidified using the same acid that was used for chlorophyllin separation. From 3 to 20 parts of solvent may be used relative to the weight of the residual solid but preferably between 6 to 10 parts. The washes are preferably conducted at ambient temperature. The solvent washes may be collected and the solvent recovered. Solvent is removed and the final solid is dried using conventional methods, preferably conducted under an inert atmosphere.

The invention may be more fully understood from the following examples:

EXAMPLE NO. 1

Approximately 660 grams of saponified marigold extract (this material contains around 72.5 grams of xanthophylls and approximately 12 grams of chlorophylls per kilogram of saponified extract) was dispersed in water at ambient temperature so as to obtain a final concentration of 10 grams per kilogram of total carotenoids in the mixture. The mixture was adjusted to pH 6 with a 25% aqueous solution of phosphoric acid. The temperature was then increased to 70° C. After 20 minutes of vigorous mixing, the mixture was allowed to rest. An aqueous bottom phase containing the potassium and magnesium chlorophyllins was produced which was easily separated. The remaining oily material was washed three more times with six volumes of the acidic aqueous solution and this removed most of the green pigments. All chlorophyllin solutions were collected together and saved for later processing.

The oily residual fraction was washed at ambient temperature for 20 minutes with a solution comprising six parts hexane to one part oil. The xanthophylls started to precipitate out of the solvent phase, which was enriched with fatty acids, carotenes and other hexane soluble lipids. The solvent was then separated by filtration and two more hexane washings were repeated in the same manner as the first. The residual solid was dried to about 4% humidity under inert gas.

A product consisting of 49 grams in weight was obtained which contained 80% of the initial pigments. This is equivalent to a concentration of 660 grams of carotenoids per kilogram of product with 92.2% lutein and 6.1% zeaxanthin which makes it very suitable for human use.

EXAMPLE NO. 2

One kilogram of saponified marigold extract (110 grams of xanthophylls and 18 grams of chlorophylls per kilogram) was dispersed in water at ambient temperature until 10 grams of carotenoids per kilogram of dispersion was obtained. The mixture was adjusted to pH 6.8 using a 15% aqueous acetic acid solution. The temperature was then increased to 60° C. with constant agitation and stirred for 30 minutes. The mixture was then allowed to rest until separation (approximately 15 minutes) and the aqueous layer was separated. The aqueous washes were repeated three more times at pH 6.8 obtaining a very faint green coloration after the fourth time.

The remaining paste was washed with a hexane:heptane mix (2:1) using eight parts of solvent per part of paste. The mix was centrifuged in a chamber bowl and the solid phase was extracted two more times removing most of the lipids. The solvent was recovered from the liquid fraction by evaporation leaving an oily residue with about 14% of the total carotenoids of the starting material. These carotenoids represented mainly carotenes, β-cryptoxanthin, epoxides from cis and trans-lutein and traces of trans-lutein. The solvent in the solid pellet from the centrifuge was eliminated by drying under nitrogen, resulting in a product with about 80% of the pigments from the raw material. The sum of lutein plus zeaxanthin represented 97.5% of the total carotenoids. The weight of the dry product was 150 grams.

EXAMPLE NO. 3

Approximately 600 grams of a marigold meal was saponified and isomerized (of the total xanthophylls 61% was zeaxanthin and 34% was lutein) according to the procedure described in U.S. Pat. No. 5,973,211 (Rodriguez); herein incorporated in its entirety by reference thereto. The resulting extract was processed as described in Example No. 1. Initially the extract had a concentration of 50 grams of total carotenoids per kilogram and 5 grams of chlorophylls per kilogram. After processing the product obtained had a concentration of 510 grams of total carotenoids per kilogram in which 66% was zeaxanthin and 33% was lutein. The final concentration and the pigment profile showed very adequate properties for human use, having little or no residual chemicals and no hazardous compounds.

EXAMPLE NO. 4

A 10 kilogram batch of saponified marigold extract (90 grams of total carotenoids and 20 grams of chlorophylls per kilogram) was mixed with water until a concentration of approximately 10 grams of xanthophylls per kilogram of mixture was obtained. The mixture was adjusted to pH 6 by adding a 10% solution of hydrochloric acid. The temperature was adjusted to 50° C. while stirring for 20 minutes. Agitation was stopped and the mixture was allowed to rest for one hour. The bottom aqueous layer containing the potassium and magnesium chlorophyllins was separated. The oily residue was washed two times with six parts water to one part extract and the aqueous layers separated for later recovery of green pigment. The semisolid remaining fraction was mixed with eight parts hexane to one part oil to yield a dispersion, which was centrifuged to form a compact sludge. This sludge was washed twice with hexane. The liquid fractions from the centrifuge were pooled and the solvent removed by evaporation under vacuum. A residue similar to the one obtained in Example No. 2 was produced and saved for incorporation in pigmenting products for the poultry industry. The solid fraction from the centrifuge still contained traces of chlorophyll-like matter. To eliminate the chlorophyll-like matter, the pellet was washed for 20 minutes with acetone acidified with phosphoric acid, pH 3 (6 parts solvent to one part solid). This resulting dispersion was filtered and the filtrant removed from the filter and washed once more with 4 parts acetone acidified to pH 3. The filtrates were collected and the solvent recovered. A green residue was obtained after removal of solvent; it was mixed with the residue from the hexane extractions for the poultry pigmenting products. Any remaining solvent in the purified solid was eliminated by drying under a nitrogen current. This yield of purified material was 85% of the carotenoids in the starting material, of which lutein and zeaxanthin comprised 97%. The weight of the final dry powder was 1.1 kilograms.

While we have described a number of embodiments of this invention, it is apparent that our description of the invention can be altered to provide other embodiments that utilize the basic process of this invention. Therefore, it will be appreciated by those of skill in the art that the scope of this invention is to be defined by the claims appended hereto rather than the specific embodiments that have been described in detail above by way of example.

What is claimed is:

1. A process for obtaining xanthophylls at a desired level of purity from a saponified extract, comprising:
   dispersing the saponified extract in water to form a dispersion;
   mixing the dispersion under conditions such that a portion of any water-soluble compounds dissolves in the water to form an aqueous phase and a residue that is not soluble in water;
   separating the aqueous phase from the residue;
   contacting the residue with a nonpolar solvent under conditions such that at least a portion of any lipid-soluble compounds dissolves in the nonpolar solvent and at least a portion of the xanthophylls precipitates from the nonpolar solvent to form a precipitate;
   separating the nonpolar solvent from the precipitate;
   washing the precipitate with a polar solvent such that at least a portion of any remaining chlorophylls dissolves in the polar solvent; and
   separating the polar solvent from the precipitate to yield a product comprising the xanthophylls at the desired level of purity.

2. The process of claim 1, wherein the saponified extract is obtained from mechanically-harvested marigolds comprising a mixture of carotenoids and chlorophylls.

3. The process of claim 1, further comprising the step of recovering a substantial portion of any carotenoids from both the nonpolar and polar solvents.

4. The process of claim 1, further comprising the steps of desolventizing and drying the product under inert atmosphere.

5. The process of claim 1, wherein prior to mixing, the dispersion is adjusted to a pH of between about 5.0 and 7.0.

6. The process of claim 5, wherein the pH is adjusted by adding an acid selected from the group consisting of phosphoric, sulfuric, hydrochloric, acetic or any mineral or organic acid of similar characteristics.

7. The process of claim 1, wherein prior to mixing, the dispersion is adjusted to a temperature of between about 45° and 80° C.

8. The process of claim 1, wherein prior to contacting the residue with the nonpolar solvent, the method further comprises washing the residue with water.

9. The process of claim 8, wherein the water used for washing is adjusted to a pH of between about 5.0 and 7.0 and a temperature of between about 45° and 80° C.

10. The process of claim 1, wherein the nonpolar solvent is selected from the group consisting of hexane, heptane, cyclohexane, octane, aromatic hydrocarbons, ethers and halogenated hydrocarbons.

11. The process of claim 1, wherein the polar solvent is selected from the group consisting of a ketone, an alcohol, an amine, and mixtures thereof.

12. The process of claim 1, wherein the xanthophylls in the product comprise a mixture of hydrolyzed lutein and zeaxanthin.

13. The process of claim 12, wherein the lutein and zeaxanthin comprise greater than 95% of the carotenoids in the saponified extract.

14. The process of claim 1, wherein the product further comprises between 400 to 900 grams of total carotenoids per kilogram of saponified extract.

15. The process of claim 1, wherein the saponified extract comprises from about 0 to 20% chlorophylls.

16. The process of claim 1, wherein a concentration of carotenoids in the dispersion is between about 0.1 to 15 grams per kilogram of the saponified extract.

17. The process of claim 1, wherein a concentration of carotenoids in the dispersion is between about 5 to 10 grams per kilogram of the saponified extract.

18. The process of claim 1, wherein the nonpolar solvent is used in a proportion of between 1 to 25 parts of solvent for each part of residue.

19. The process of claim 1, wherein the nonpolar solvent is used in a proportion of between 5 to 12 parts of solvent for each part of residue.

20. The process of claim 1, wherein the polar solvent is used in a proportion of between 1 to 15 parts of solvent for each part of precipitate.

21. The process of claim 1, wherein the polar solvent is used in a proportion of between 4 to 10 parts of solvent for each part of precipitate.

22. The process of claim 1, wherein both the nonpolar and polar solvents are used at ambient temperature.

23. The process of claim 1, wherein the product is further characterized in that it is suitable for administration to humans.

24. A process for obtaining xanthophylls at a desired level of purity, comprising:
   obtaining a saponified extract of a mechanically-harvested plant composition, said composition comprising a first plant part which comprises xanthophylls and a second plant part which comprises chlorophylls;

washing the saponified extract with water leaving an oily residue;

contacting the residue with a nonpolar solvent under conditions such that at least a portion of any lipid-soluble compounds dissolves in the nonpolar solvent and at least a portion of the xanthophylls precipitates from the nonpolar solvent to form a precipitate;

separating the nonpolar solvent from the precipitate;

washing the precipitate with a polar solvent such that at least a portion of any remaining chlorophylls dissolves in the polar solvent; and separating the polar solvent from the precipitate to yield a product comprising the xanthophylls at the desired level of purity.

* * * * *